(12) United States Patent
Roberts et al.

(10) Patent No.: US 9,202,295 B2
(45) Date of Patent: Dec. 1, 2015

(54) FIELD OF IMAGING

(75) Inventors: Paul Roberts, Cambridge (GB); Andrew Maiden, Sheffield (GB)

(73) Assignee: PHASE FOCUS LIMITED, Sheffield, South Yorkshire (GB)

( * ) Notice: Subject to any disclaimer, the term of this patent is extended or adjusted under 35 U.S.C. 154(b) by 1196 days.

(21) Appl. No.: 13/121,064

(22) PCT Filed: Sep. 23, 2009

(86) PCT No.: PCT/GB2009/051243
§ 371 (c)(1),
(2), (4) Date: Jun. 7, 2011

(87) PCT Pub. No.: WO2010/035033
PCT Pub. Date: Apr. 1, 2010

(65) Prior Publication Data
US 2011/0235862 A1    Sep. 29, 2011

(30) Foreign Application Priority Data
Sep. 26, 2008  (GB) .................................. 0817650.5

(51) Int. Cl.
*A61B 6/00* (2006.01)
*G01N 23/20* (2006.01)
*G06T 11/00* (2006.01)
*A61B 6/12* (2006.01)
*G06T 1/20* (2006.01)

(52) U.S. Cl.
CPC .................. *G06T 11/006* (2013.01); *A61B 6/52* (2013.01); *G01N 23/20* (2013.01); *A61B 6/12* (2013.01); *G06T 1/20* (2013.01)

(58) Field of Classification Search
CPC .......... A61B 6/12; A61B 6/52; A61B 6/5205; G06T 1/20
See application file for complete search history.

(56) References Cited

U.S. PATENT DOCUMENTS 6,005,916 A * 12/1999 Johnson et al. ................. 378/87
6,226,353 B1 * 5/2001 Wilkins et al. ............... 378/98.9

FOREIGN PATENT DOCUMENTS

| JP | 2007-534956 A | 11/2007 |
| JP | 2010-528279 A | 8/2010 |
| WO | 2005106531 | 11/2005 |

OTHER PUBLICATIONS

Thibault et al., "High-Resolution Scanning X-ray Diffraction Microscopy", Science, Jul. 18, 2008, vol. 321, pp. 379-382.
International Preliminary Report on Patentability in corresponding PCT application No. PCT/GB2009/051243 dated Mar. 29, 2011.
Frigo et al., "The Design and Implementation of FFTW3," IEEE, vol. 93, No. 2, 2005, pp. 216-231.
Rodenburg et al., "Hard X-Ray Lensless Imaging of Extended Objects," The American Physical Society, Physical Review Letters, Jan. 19, 2007, pp. 034801-1 to 034801-4.
Rodenburg et al., "Transmission Microscopy Without Lenses for Objects of Unlimited Size," Science Direct, Ultramicroscopy 107, (2007), pp. 227-231.

* cited by examiner

*Primary Examiner* — Thomas R Artman
(74) *Attorney, Agent, or Firm* — Lando & Anastasi, LLP (57) ABSTRACT

Embodiments of the present invention provide a computer-based method for providing image data of a region of a target object (31), comprising the steps of estimating (706) a first intermediate object function indicating at least one characteristic of a first sub-region (501, 503) of said region of the target object, estimating (706) a second intermediate object function indicating at least one characteristic of a second sub-region (502, 504) of said region of the target object, and combining (707) the first and second intermediate object functions to form a combined object function indicating at least one characteristic of the region of the target object (31).

21 Claims, 7 Drawing Sheets

FIELD OF IMAGING

The present invention relates to an improved method and apparatus for providing image data from which an image of a target object may be generated.

WO 2005/106531, which is herein incorporated by reference for all purposes, discloses a method and apparatus for producing high resolution images of a region of a target object. In the disclosed apparatus and method, incident radiation is caused to fall upon the target object and is scattered as it passes through and beyond the target object, causing a wave function of the incident radiation to be modified in both amplitude and phase with respect to the wave function of the incident radiation at a pre-target side of the object. An array of detectors, such as a CCD detector, is arranged a suitable distance from the target object and a diffraction pattern is formed by propagation to a diffraction plane. In one embodiment, an aperture is located post-object to select an area of the target object for investigation. In another embodiment, a weakly focussing lens is used to illuminate an area of the object.

Using the formed diffraction pattern as input data measured by the array of detectors and knowledge of a probe function formed by the aperture or weakly focussing lens an algorithm is utilised to determine an object function in the form of a two dimensional complex function for the target object. The algorithm is explained in WO 2005/106531 particularly with reference to FIG. 7 of that document. As will be appreciated, the algorithm requires repeated iteration until a predetermined event occurs. For example, the iteration may be repeated 1000 times or until a sum squared error (SSE) is sufficiently small. Repetition of the algorithm represents a significant processing requirement which even on a relatively fast processor takes an appreciable processing time. For example, tests using a PC with an Intel "Core2 2 GHz" central processing unit (CPU) have shown that a single iteration of the method takes 85 seconds for a set of 64 1000×1000 pixel diffraction patterns. Typically 10 iterations of the method may be required to produce a high-resolution image which takes around 14 minutes. It is desired to overcome, or at least reduce, this problem.

An aim of embodiments of the present invention is to allow the production of image data in a shorter period of time, from which images, including high resolution images may optionally be produced.

It is an aim of embodiments of the present invention to provide a method and apparatus for generating, in a relatively shorter period of time, a wavelength-limited image data.

According to a first aspect of the present invention, there is provided a computer-based method for providing image data of a region of a target object, comprising the steps of: estimating a first intermediate object function indicating at least one characteristic of a first sub-region of said region of the target object; estimating a second intermediate object function indicating at least one characteristic of a second sub-region of said region of the target object; and combining the first and second intermediate object functions to form a combined object function indicating at least one characteristic of the region of the target object.

According to a second aspect of the present invention, there is provided a method of providing image data of a region of a target object without high resolution positioning of incident radiation or a post target object aperture relative to the target object, comprising the steps of: providing incident radiation, from a radiation source, at the target object; via at least one detector, detecting the intensity of radiation scattered by said target object; responsive to the detected intensity, estimating first and second intermediate object functions indicating at least one characteristic of first and second sub-regions, respectively, of said region of the target object; and combining the first and second object functions to form a combined object function indicating at least one characteristic of the region of the target object.

According to a third aspect of the present invention, there is provided an apparatus for providing image data relating to a region of a target object, comprising: a first computational unit arranged to estimate a first intermediate object function indicating at least one characteristic of a first sub-region of said region of the target object; and a second computational unit estimating a second intermediate object function indicating at least one characteristic of a second sub-region of said region of the target object; wherein a computational unit is arranged to combine the first and second object functions to form a combined object function indicating at least one characteristic of the region of the target object.

According to a fourth aspect of the present invention, there is provided an apparatus for providing image data for generating an image of a region of a target object, comprising: locating means for locating a target object at a predetermined location; a radiation source for providing incident radiation at a target object located by said locating means; at least one detector device for detecting an intensity of radiation scattered by said target object; radiation locating means for locating incident radiation or an aperture, located post target object, at one or more locations with respect to said target object; first processing means for determining a first intermediate object function responsive to a detected intensity of scattered radiation from a sub-region of the target object comprising one or more areas selected by the radiation locating means; and second processing means for determining a second intermediate object function responsive to a detected intensity of scattered radiation from a sub-region of the target object comprising one or more areas selected by the radiation locating means; wherein one of the first or second processing means, or a third processing means, is arranged to combine the first and second object functions to form a combined object function indicating at least one characteristic of the region of the target object.

Embodiments of the present invention reduce an object function computation time by employing parallel processing. Two or more computational units are each utilised to compute an intermediate object function. After computation of the intermediate object functions a computational unit combines the intermediate object functions to form an estimate of the object function for that iteration. In a subsequent iteration, the two or more processing units utilise the previous estimate of the object function to again form intermediate object functions, which are then combined by a computational unit to form the following iteration's estimate of the object function. In this way, parallel processing of intermediate object functions is utilised. However a disparity between object functions estimated for individual regions does not occur, or at least is minimised, by frequent combination of intermediate object function estimates.

Embodiments of the invention will now be described by way of example only, with reference to the accompanying figures, in which.

In the drawings, like reference numerals refer to like parts.

Before discussing embodiments of the present invention, a brief introduction to a prior art apparatus, method and algorithm as disclosed in WO 2005/106531, which is incorporated herein in its entirety by reference for all purposes, will be provided. The embodiment of the prior art discussed is a moving aperture arrangement as disclosed in WO 2005/106531. However, it will be realised that a prior art method of moving a weakly focussing lens is also known and that embodiments of the present invention may also be used in conjunction with such an arrangement of weakly focussing lens. Further, embodiments of the present invention may also be used with a pre-target aperture to illuminate an area of the object.

Figure 1:
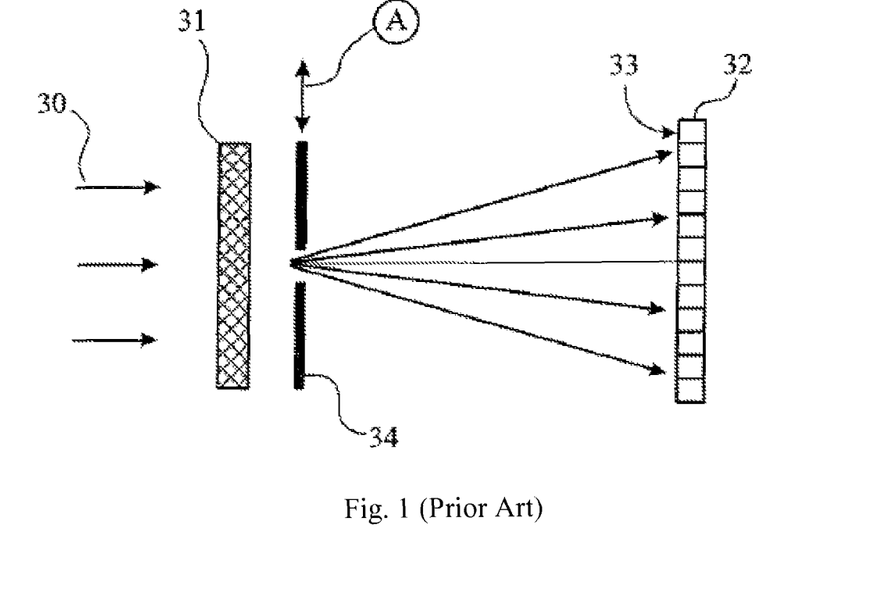
FIG. 1 shows a moving aperture arrangement known from the prior art.

Referring to FIG. 1, a prior art arrangement is shown in which incident radiation 30 is caused to fall upon a target object 31.

It will be understood that the term target object refers to any specimen or item placed in the path of incident radiation which causes scattering of that radiation. It will be understood that the target object should be at least partially transparent to incident radiation. The target object may or may not have some repetitive structure.

It is to be understood that the term radiation is to be broadly construed as energy from a radiation source. This will include electro magnetic radiation including X-rays, emitted particles such as electrons and/or acoustic waves. Such radiation may be represented by a wave function $\Psi(r)$. This wave function includes a real part and an imaginary part as will be understood by those skilled in the art. This may be represented by the wave functions modulus and phase. $\Psi(r)^*$ is the complex conjugate of $\Psi(r)$ and $\Psi(r) . \Psi(r)^* = |\Psi(r)|^2$ where $|\Psi(r)|^2$ is an intensity which may be measured for the wave function.

The incident radiation 30 is scattered as it passes through and beyond the target object 31. As such the wave function of the incident radiation as it exits the target object 31 will be modified in both amplitude and phase with respect to the wave function of the incident radiation at the pre-target side of the target object 31. The scattering which occurs may include Fourier diffraction, refraction and/or Fresnel diffraction and any other form of scattering in which characteristics of the incident radiation are modified as a result of propagating after the target object 31. If an array of detectors such as a CCD detector 32 is arranged a long distance from the target object 31 then a diffraction pattern is formed at a diffraction plane 33. A Fourier diffraction pattern will form if the detectors 32 are located a distance D from the target object 31 where D is sufficiently long for the diffraction pattern to be formed effectively from a point source. If the diffraction plane is formed closer to the target object 31, by locating the detectors nearer, then a Fresnel diffraction pattern will be formed. An aperture 34 is located post target object to thereby select a region of the target for investigation. The aperture is formed in a mask so that the aperture defines a "support". A support is an area of a function where that function is not zero. In other words outside the support the function is zero. Outside the support the mask blocks the transmittance of radiation. Apertures for use with the present invention need not be finite and sharply defined. They may be moveable and slowly varying at their edges. In this way the softly varying illumination function or transmittance is not composed of high spatial frequencies. In other words it is a bandwidth limited function. As no lens is used a large field of view may be measured by the detectors 32. The term aperture describes a localised transmission function of radiation. This may be represented by a complex variable in two dimensions having a modulus value between 0 and 1. An example is a mask having a physical aperture region of varying transmittance.

Figure 2:
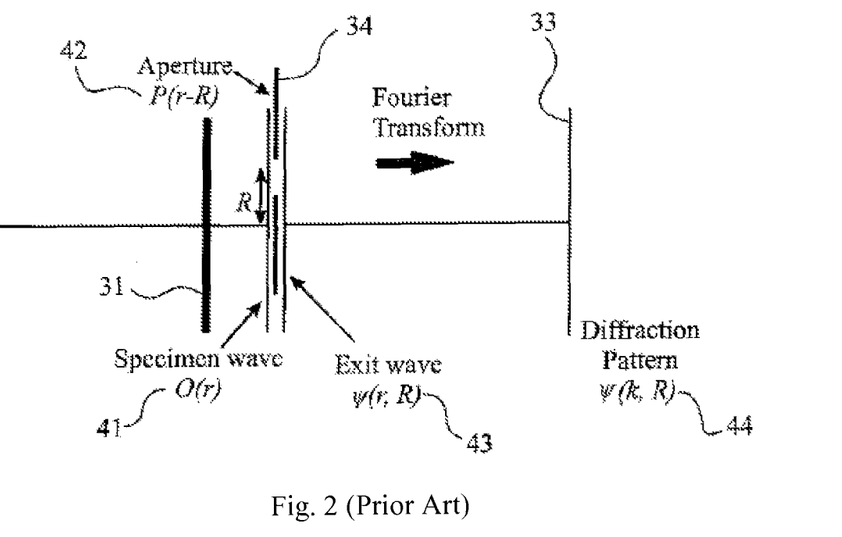
FIG. 2 shows an illustration of moving a post-target aperture known from the prior art.

FIG. 2 illustrates schematically the propagation of waves through the arrangement of FIG. 1. Incident radiation 30 falls upon the up-stream side of the target object 31 and is scattered by the target object 31 as it is transmitted. A target object wave O(r) is an exit wave function of radiation after interaction with the target object 31. In this way O(r) represents a two-dimensional complex function so that each point in O(r), where r is a two-dimensional coordinate, has associated with it a complex number. O(r) will physically represent an exit wave that would emanate from the target object 31 which is illuminated by a plane wave. For example, in the case of electron scattering, O(r) would represent the phase and amplitude alteration introduced into an incident wave as a result of passing through the target object 31 of interest. The aperture 34 provides a probe function P(r) (or filtering function) which selects a part of the object exit wave function for analysis. It will be understood that rather than selecting an aperture a transmission grating or other such filtering function may be located downstream of the object function. The probe function P(r–R) is an aperture transmission function where an aperture is at a position R. The probe function can be represented as a complex function with its complex value given by a modulus and phase which represent the modulus and phase alterations introduced by the probe into a perfect plane wave incident up it.

The exit wave function $\psi(r,R)$ 43 is an exit wave function of radiation as it exits the aperture 34. This exit wave $\Psi(r,R)$ 43 forms a diffraction pattern $\Psi(k,R)$ 44 at a diffraction plane 33. Here r is a vector coordinate in real space and k is a vector coordinate in diffraction space.

Figure 3:
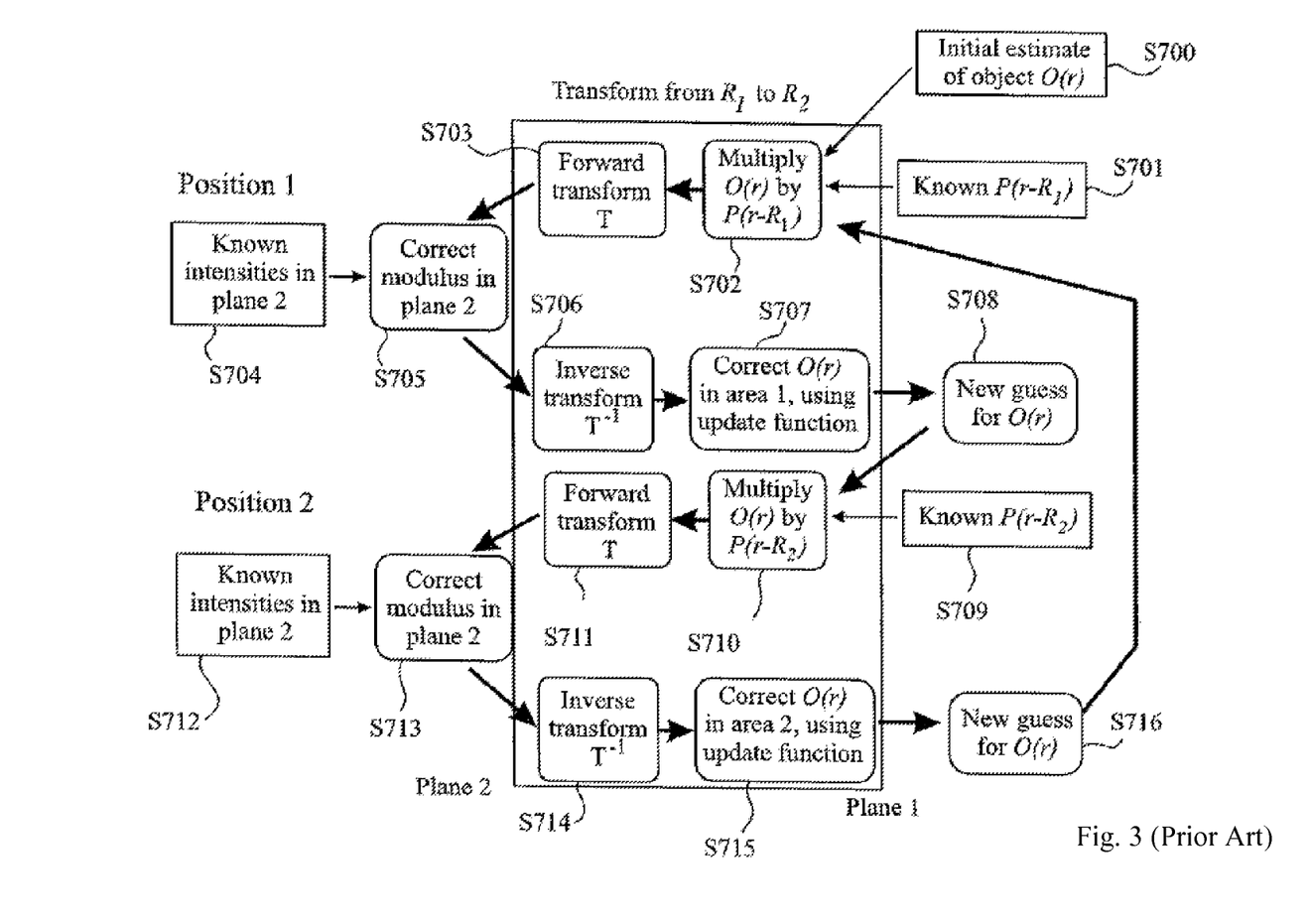
FIG. 3 shows illustrates a prior art phase retrieval algorithm.

FIG. 3 illustrates a prior art algorithm for obtaining a wave function of an object and thus for obtaining image data which may be used subsequently to generate high resolution images of an object. FIG. 3 illustrates a method using the arrangement illustrated in FIGS. 1 and 2 and moving the aperture from a first position after measuring the diffraction pattern to a second position where a second respective diffraction pattern may be measured.

As noted above O(r) and P(r) represent two-dimensional complex functions, that is, each point in O(r) or P(r), where r is a two-dimensional coordinate, has associated with it a complex number. In what follows, O(r) will physically represent an exit wave that would emanate from an object function which is illuminated by a plane wave. For example, in the case of electron scattering, O(r) would represent the phase and amplitude alteration into an incident wave as a result of passing through the object of interest.

In what follows P(r) represents either an illumination function, such as that generated by a caustic or illumination profile formed by a lens or other optical component or a filtering function, such as an aperture or transmission grating mounted downstream of the object function.

It may be assumed in what follows that O(r) or P(r) can be moved relative to one another by various distances R. The nomenclature adopted is written in terms of moving P(r), although equivalently we could instead move O(r) relative to P(r). In both situations, the complex value of O(r) is altered by forming the product of O(r) with P(r−R) to give a total exit wave function of ψ(r), i.e.

$$\psi(r,R) = O(r)P(r-R) \tag{1}$$

The algorithm works to find the phase and intensity of the complex function ψ(r,R). It requires as input knowledge of the function P(r−R), and one or more (preferably several) measurements of the intensity of the wave function in a plane which is different to that containing the target object 31. It is convenient to use the diffraction plane, which is related to the specimen plane by the Fourier transform. In this case the measured input data is the intensities of the diffraction patterns at one or more probe/aperture positions. However it is also possible to run the algorithm based on a set of defocused images measured at some distance from the exit surface of the specimen/aperture. In this situation the free space propagator is substituted for the Fourier transform. The algorithm is not restricted to use of these two transforms. Other effective transforms could be used to move from one plane of information to the other. In what follows a general transform T is referred to that transforms a wave function from the first plane, called plane 1, to the second plane, called plane 2.

The algorithm works as follows and with reference to FIG. 3:

1. Start at step S700 with a guess at the object function $O_{g,n}(r)$, where the subscript g,n represents a guessed wave at the nth iteration of the algorithm. These functions are in plane 1 (which is the real space plane if the Fourier transform is used). The first guess of $O_{g,n}(r)$ may equal unity at all points r. This corresponds to an absent specimen. Alternatively, $O_{g,n}(r)$ may be set to a random values at each point.

2. A known aperture in terms of position and characteristics is selected at step S701. This provides a probe function P(r−R). At step S702 the current guess at the object function is multiplied by the aperture or probe at the current position R, P(r−R). This produces the guessed exit wave function (still in plane 1) for position R, $$\psi_{g,n}(r,R) = O_{g,n}(r)P(r-R) \tag{2}$$

3. Next at step S703 a transformation of $\psi_{g,n}(r,R)$ to obtain the corresponding wave function in plane 2 (which would be the diffraction space plane if the Fourier transform is used), for that position R. Here T is used to represent some general transform that would often be the Fourier transform, but could also be the Fresnel free space propagator, or some other transform suited to a particular application of the algorithm.

$$\Psi_{g,n}(k,R) = T[\psi_{g,n}(r,R)] \tag{3}$$

k is the coordinate in plane 2. (For the Fourier transform, k would be the usual reciprocal space coordinate. For the propagator, k would be the xy coordinate in the defocused plane.) It is important to note that $\Psi_{g,n}(k,R)$ is a "guessed" version of the actual wave function in plane 2, since it has been produced by the guessed object function $O_{g,n}(r)$. Successive iterations of the algorithm will produce increasingly accurate versions of $\Psi_{g,n}(k,R)$.

Note that $\Psi_{g,n}(k,R)$ can be written in the form:

$$\Psi_{g,n}(k,R) = |\Psi_{g,n}(k,R)| e^{i\theta_{g,n}(k,R)} \tag{4}$$

where $|\Psi_{g,n}(k,R)|$ is the (guessed) wave function amplitude and $\theta_{g,n}(k,R)$ is the (guessed) phase in plane 2 at iteration n, for position R.

By measuring the intensity of the diffraction pattern by known techniques such as detector array 32 information about the actual transformed exit wave function are known. A measured intensity of the diffraction pattern where the aperture is in a first position thus forms the basis of an estimate of the complex wave function of the diffraction pattern. However the measured intensity does not provide information about the phase of the wave function. Rather the measured intensity is comparable to the squared modulus of Ψ(r). That is $|\Psi(r)|^2$. Once the intensity of radiation in the diffraction pattern in plane 2 is known at step S704 then the following step may be carried out.

4. Correct, at step S705 the intensities of the guessed plane 2 wave function to the known values.

$$\Psi_{C,n}(k,R) = |\Psi(k,R)| e^{i\theta_{g,n}(k,R)} \tag{5}$$

where $|\Psi(k,R)|$ is the known plane 2 modulus. That is the square root of the measured intensity at the image plane.

5. Inverse transform S706 back to real space to obtain a new and improved guess at the exit wave function (in plane 1) ($T^{-1}$ represents the inverse of the previously used transform T), $$\psi_{C,n}(r,R) = T^{-1}[\Psi_{C,n}(k,R)] \tag{6}$$

6. Update via step S707 the guessed object wave function in the area covered by the aperture or probe, using the update function:

$$O_{g,n+1}(r) = O_{g,n}(r) + |P(r-R)|P^*(r-R)\beta(\psi_{C,n}(r,R) - \psi_{g,n}(r,R))|P\max(r-R)|l(|P(r-R)|^2 + \delta) \tag{7}$$

where the parameters β, δ and l are appropriately chosen, and $|P\max(r-R)|$ is the maximum value of the amplitude of P(r). The result is a new guess for the object function (S708).

The update function helps make the effective deconvolution that occurs possible and introduces a weighting factor which causes the object function to be updated most strongly where the probe function has largest amplitude. The selectable constant l may be set to 1. It may be selected as any value in the range of 0 to 3 and need not be an integer value. It is useful to set l>1 when there is much noise. l may be selected l<1 when because of scattering geometry, the detected intensity is of the form of a Gabor hologram or similar. The value δ is used to prevent a divide-by-zero occurring if |P(r−R)|=0. δ is a small real number as is commonly applied in Weiner Filters and is usually (though not necessarily) smaller than Pmax and can be considerably smaller if the noise present in the recorded data is small. The constant β controls the amount of feedback in the algorithm, and may advantageously be varied between roughly 0.1 and 1. When β=less than 0.5, the previous estimate of the object is considered to be more important than the new estimate. Values in between vary the relative importance of the two estimates. β determines how quickly a solution is reached.

δ is a parameter which may be set at a fixed value or which may vary. It indicates how noisy the recorded data is and is used to attenuate how the updating is carried out in response to these circumstances. If good conditions exist for data collection that is to say with high beam current (high flux), which would imply low shot-noise, then it is safer to use results gathered to update the guessed estimate. Consequently the value of δ can be a small fraction of Pmax (e.g. less than 1/10th).

The expression:

$$\frac{|P(r-R)|l}{|P\max(r-R)|l} \tag{8}$$

maximises the update effect of regions where |P(r−R)| is large. This is useful, since it is those regions which are receiving the highest amount of incident radiation, and therefore which contain information with a relatively high signal to noise ratio. This information is clearly more valuable than that from regions where very little radiation is incident, and which is heavily affected by noise.

For the situation where β=1, l=0 and δ=0, and the function P(r−R) is a mask that is can be represented by a region where its value is unity while it is zero elsewhere, or support function, the algorithm has some similarities to the well known Fienup algorithm. If in this situation, only one position R is used, then the algorithm reduces to being mathematically identical to the basic Fienup algorithm. Where more than one position R is used, the algorithm has considerable advantages over known methods, including the fact that it does not suffer from uniqueness issues, and that a wider field of view may be imaged.

Figure 7A:
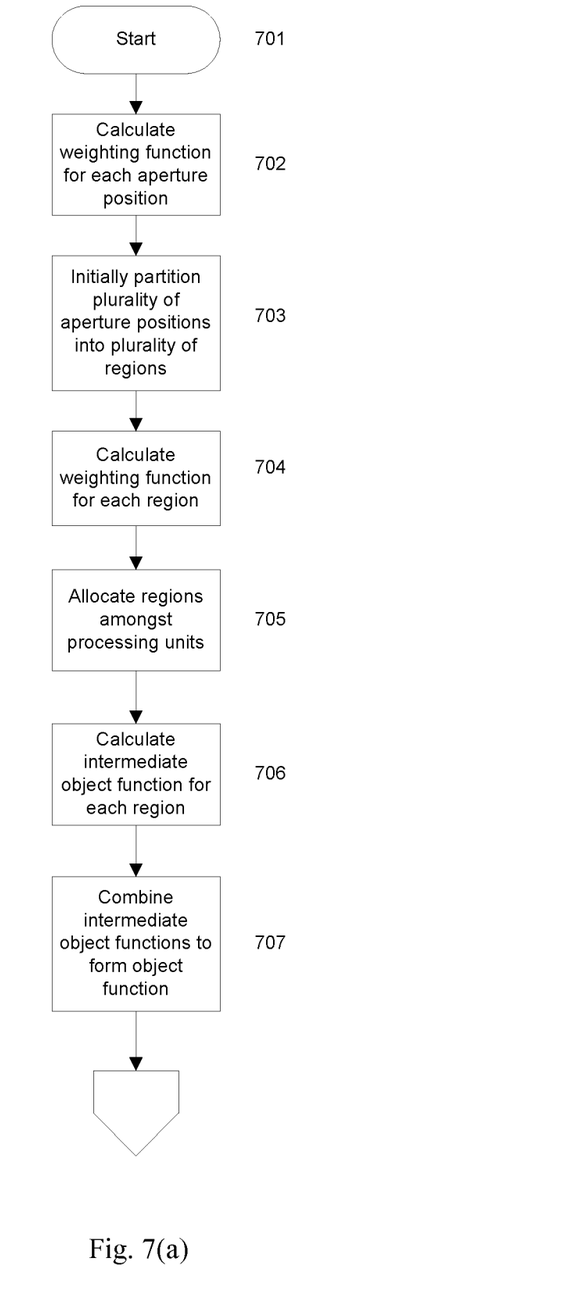
FIG. 7 shows an illustration of a second embodiment of a method according to the present invention.
Figure 7B:
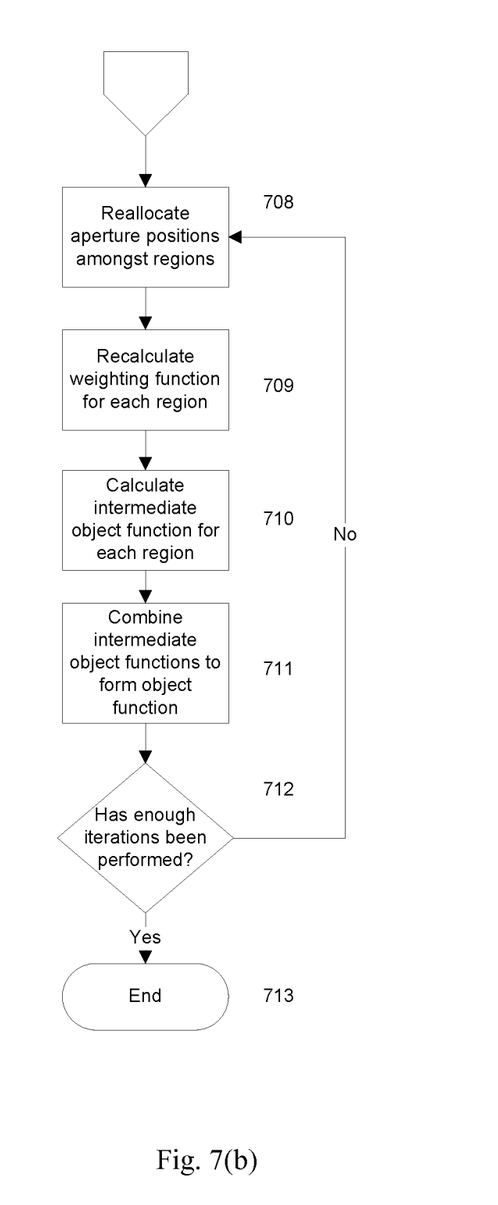

Subsequent to updating the running estimate of the guess the algorithm shown in FIG. 7 progresses to selecting a new position R which at least in part overlaps the previous position. The overlap should preferably be more than 20% and is preferably 50% or more. This may be achieved by moving the aperture in the direction of arrow A shown in FIG. 1 by a predetermined amount or by causing the illuminating radiation to fall upon a different region of the target. It will be understood that image data for one location of a target object may be provided without any change in location of an aperture or incident radiation being made. In such embodiments after step S708 the algorithm returns to step S702. Instead of the initial estimate of the object function O(r) being loaded in the new guess for O(r) of step S708 is loaded in. On each iteration the new guess for the object function will approximate closer and closer to the actual object function as on each iteration information of the known intensity and thus the known amplitude component of the incident radiation is added to improve the accuracy of the estimate.

Nevertheless the more preferable method is to move to a new position R which in part overlaps the previous position as shown in FIG. 3.

A known probe function P(r−R$_2$) at the second position is identified at step S709 and then the step as above mentioned are repeated so that the new guess generated in step S708 is multiplied with the new known probe function identified at step S709. This is illustrated in step S710. Effectively this generates an exit wave function either post specimen or post aperture depending upon the embodiment concerned. The resulting exit wave function is propagated at step S711 to provide an estimate of the scattering pattern which should be detected at that position. The diffraction pattern is measured at step S712 which provides intensity information and thus amplitude information about the transformed wave function. The intensity information is used to correct the amplitude of the transformed wave function whilst phase information is retained at step S713. This corrected wave function is inversely propagated via Fourier transformation (when the image is formed in the far field), Fresnel transformation when the image is formed at a location where Fresnel diffraction dominates or by any other suitable transformation. This is illustrated at step S714. The running estimate of O(r) is then corrected according to the update function shown above at step S715 and the result is a new guess for the object function illustrated in step S716.

At this stage further movement of the illumination or aperture may be made to a third or further position. Again a location where some overlap occurs between previous illuminated locations is preferable. In this way the whole target object may optionally be mapped. Alternatively the new guess generated at step S716 may be repeated without further positioning knowing known diffraction pattern results. In FIG. 3 the iterative method is illustrated as being repeated by returning to step S702 in which the new guess generated at step S716 is input to the multiplication stage rather than the initial estimate of the object function supplied at step S700.

The iterative method may be repeated until a predetermined event occurs. For example the iteration may be repeated a predetermined number of times, for example 1000 times or until the sum squared error (SSE) is sufficiently small. The SSE is measured in plane 2, as $$SSE = \frac{(|\psi g, n(k, R)|^2 - |\psi(k, R)|^2)^2}{N} \quad (9)$$

where N is the number of pixels in the array representing the wave function.

During the iteration process the most up-to-date guess of the object function provides a running estimate for that object function. When the iteration process is completed as determined by the occurrence of a predetermined event, the running estimate of the object function provides image data at the locations which are either illuminated by the incident radiation or which are selected by location of a post target object aperture. This image data includes amplitude and phase information which can subsequently be used to generate a high resolution image of the selected region of the target object.

However, as noted above, running the above algorithm a large number of times, e.g. 1000 times, represents a significant computational load which takes an appreciable computation time. A method and algorithm which enables faster computation of an object function will now be described.

Embodiments of the algorithm according to the present invention operate on diffraction patterns formed with an aperture at different n positions R$_1$ ... R$_n$, where n is two or more. It will also be realised that embodiments of the algorithm may also be applied to diffraction patterns formed by radiation incident upon different regions of a target object 31. As noted above, each aperture position should at least in part overlap a previous aperture position, preferably by at least 20% or more and more preferably by at least 50%.

Figure 4:
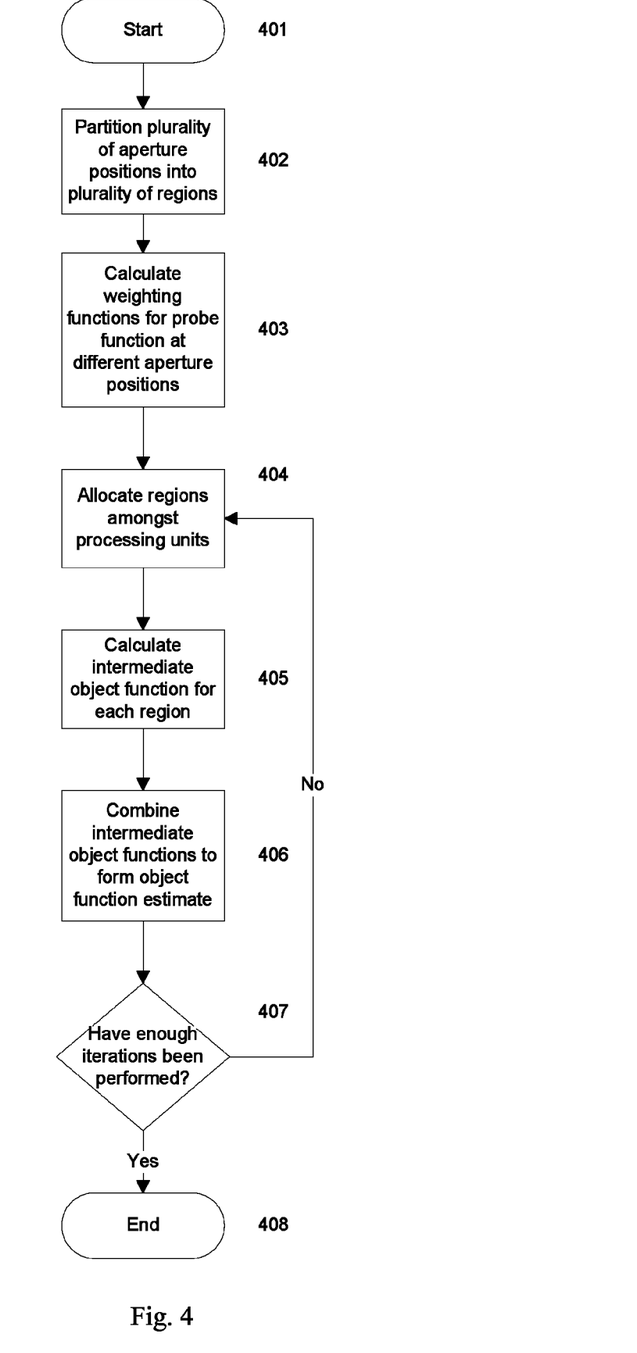
FIG. 4 shows an illustration of a first embodiment of a method according to the present invention.

As shown in FIG. 4, the method begins in step 401.

In step 402, the n aperture positions: R$_1$ ... R$_n$ are partitioned into, or allocated amongst, m regions: S$_1$ ... S$_m$. It is not necessary to partition the m regions so that each contains the same number of aperture positions, although doing so will lead to the fastest overall computational time. In some embodiments, the m regions may contain each aperture position exactly once, i.e. the union of all m regions is exactly R$_1$ ... R$_n$.

Figure 5:
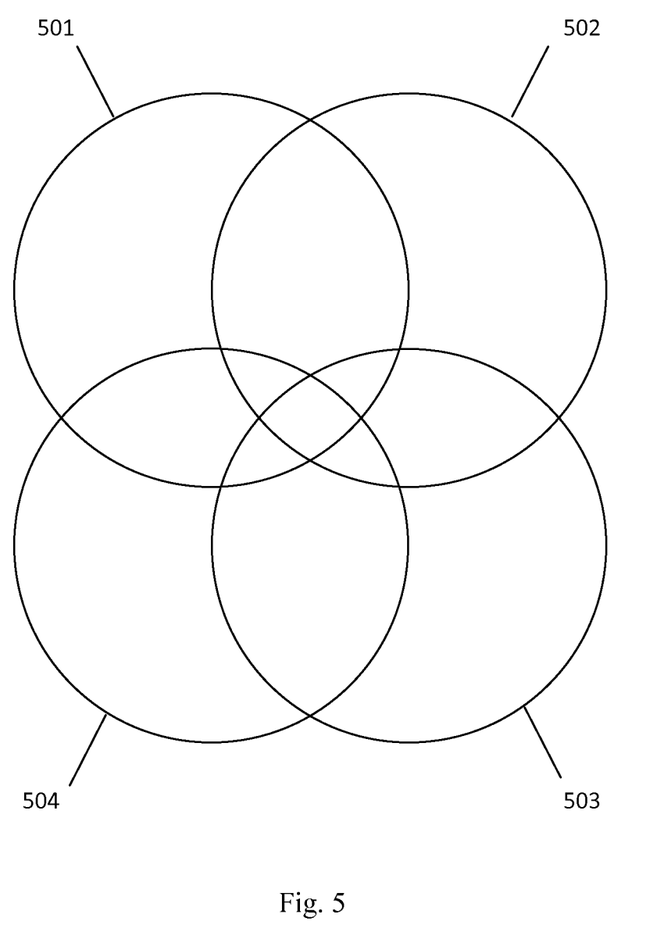
FIG. 5 schematically illustrates four aperture positions.

An example will be described to illustrate embodiments of the present invention which uses four different aperture positions R$_1$ ... R$_4$ which are grouped into two regions S$_1$,S$_2$. Therefore, n=4 and m=2 in the example. FIG. 5 shows an illustration of the four regions 501-504, wherein R$_1$=501, R$_2$=502, R$_3$=503 and R$_4$=504. It will be noted that the shape and arrangement of the four regions is merely an example and their degree of overlap is merely shown for illustration. In step 402, the four aperture positions R$_1$ ... R$_4$ are divided into the two regions S$_1$,S$_2$ such that S$_1$ comprises R$_1$ and R$_3$, whilst S$_2$ comprises aperture positions R$_2$ and R$_4$. It will be noted that the aperture positions have been arbitrarily assigned to the regions. For example, S$_1$ could comprise aperture positions R$_1$ and R$_4$ and no inter-relationship, such as a positional relationship, between regions and aperture positions is required.

In step 403, a weighting function w$_N$(r−R) pertaining to the probe function at different aperture positions is calculated for each aperture position. A weighting function for each region $w_S(r, S_m)$ is then calculated. The purpose of weighting is to cause the object function to be updated most strongly where the probe function has the largest amplitude i.e. carries more information.

In more detail, a total weight for all aperture positions is calculated as follows:

$$W_t(r) = \sum_{R=R_1...R_n} w(r-R) \qquad (10)$$

where there are n different aperture positions and w(r−R) is the individual weighting factor for a particular aperture position R and is given by:

$$w(r-R) = \beta \frac{|P(r-R)|^l}{|P_{max}(r-R)|^l} \qquad (11)$$

This weighting factor is identical in definition and meaning to that found in the prior art, wherein the weighting factor is not a scalar variable but instead causes the object function to be updated most strongly where the probe function has largest amplitude. The weighting factor is essentially a normalized version of the probe function modified by β and l as shown above.

A normalized weighted probe function at all aperture positions is then calculated by:

$$w_N(r, R) = \begin{cases} \dfrac{w(r-R)}{W_t(r)} & \text{for } W_t(r) \neq 0 \\ 0 & \text{otherwise} \end{cases} \qquad (12)$$

The purpose of conditional assignment of $w_N(r-R)$ is to prevent a divide-by-zero occurring if $W_t(r)=0$.

For each of the m regions a weighting function is calculated by:

$$w_S(r, S_m) = \sum_{R \in S_m} w_N(r, R) \qquad (13)$$

where $S_m$ is the mth region.

So, for the example, the weighting of region $S_1$ is given by:

$$w_S(r,S_1) = w_N(r,R_1) + w_N(r,R_3) \qquad (14)$$

whilst the weighting of region $S_2$ is given by:

$$w_S(r,S_2) = w_N(r,R_2) + w_N(r,R_4) \qquad (15)$$

In some embodiments, Equations 10-12 used to calculate aperture position weighting functions may be pre-calculated apriori. That is, the weighting functions may be determined in advance before the algorithm is desired to begin, thus saving computation time. In the first embodiment, Equations 13-15 may also be calculated in advance since the allocation of aperture positions amongst regions does not change during iterations of the algorithm.

In step 404, calculation of an intermediate object function for each region is assigned to a computation unit selected from amongst two or more computational units. During repeated iterations of the algorithm, intermediate object functions for each region will be repeatedly calculated. Whilst it may be more convenient to assign the calculation of an intermediate object function to a particular computational unit throughout the repeated iterations, the algorithm is not constrained in this way. That is, a first computational unit may calculate an intermediate object function for region $S_1$ during a first iteration and the calculation of an intermediate objection function for region $S_1$ during a second iteration may be performed by a second computational unit.

The term computational unit is understood to mean a unit capable of performing independent calculations. For example, an individual processor may represent a computational unit. However, a core of a multi-core processor may also represent a computational unit. A combination of cores in a multi-core processor or individual processor architectures may also be used. Furthermore, the computational units may be local to one-another i.e. connected to a bus interconnect, or may be remotely located and connected together by a wired or wireless communications medium, such as a network e.g. LAN or WAN network.

In one embodiment, each computational unit calculates an intermediate object function for a respective region. However, in other embodiments one or more computational units may calculate intermediate object functions for more than one region, depending upon a speed of execution of those computational units. It will be understood that it would be preferable to balance computing load across the computational units such that each computational unit finishes calculating intermediate objection functions for the one or more regions which it has been allocated at approximately the same time as the other computational units. This allows computational units having different speeds of execution to be used in combination.

Figure 6:
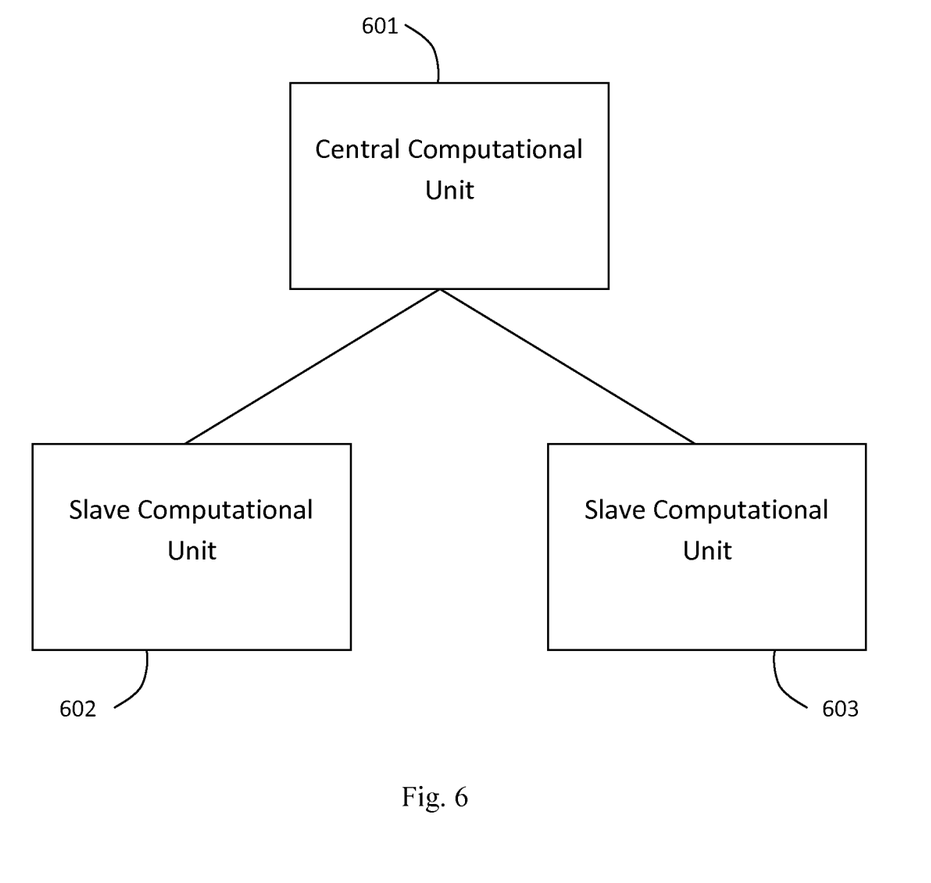
FIG. 6 schematically illustrates an arrangement of computational units of an embodiment of the present invention.

As an example, an arrangement is shown in FIG. 6 comprising a central computational unit and two slave computational units 602, 603. In the example, the central computational unit is responsible for performing steps 402-404 of the method illustrated in FIG. 4, whilst each of the slave computational units 602, 603 calculates in parallel an intermediate object function for each region $S_1$, $S_2$ of the described example. The designations "central" and "slave" do not imply any functional inter-dependency of the slave computational units 602, 603 on the central computational unit 601 or any performance hierarchy amongst the computational units. For example, the central computational 601 unit may be identical to the slave computational units 602, 603. Furthermore, whilst the example arrangement is being used for illustration with respect to two regions $S_1$, $S_2$ for each of which an intermediate objection function will be calculated by a respective slave computational unit 602, 603 and the intermediate object functions used by the central computational unit 601 to calculate an object function or combined object function for each iteration, it will be realised that the central computation unit 601 may calculate an intermediate object function for one region and then calculate the combined object function using an intermediate objection calculated for the other region by one of the slave computational units 602, thus reducing the number of slave computational units required.

In step 405, computational units calculate in parallel intermediate object function guesses for all of the regions.

For each region, the algorithm of WO 2005/106531 is applied which comprises starting with an object function guess and a known probe function and multiplying the two to form a guessed exit wave function in first plane; transforming that exit wave function to form an exit wave function in a second plane which is then corrected against measured intensities of the wave function in the second plane before inversely transforming the function to obtain an improved guess of the exit wave function in the first plane as explained with reference to steps 700-706 in particular. For more information, the reader is referred to FIG. 3 and WO 2005/106531.

WO 2005/106531 gives the equation used to update an object function guess for a j+1$^{th}$ iteration as:

$$O_{g,j+1}(r) = \qquad (16)$$
$$O_{g,j}(r) + \frac{|P(r-R)|^l P^*(r-R)}{|P_{max}(r-R)|^l (|P(r-R)|^2 + \delta)} \beta(\psi_{c,j}(r,R) - \psi_{g,j}(r,R))$$

This may be re-written as:

$$O_{g,j+1}(r) = O_{g,j}(r) + \qquad (17)$$
$$w(r-R)\left(\frac{P^*(r-R)}{|P(r-R)|^2 + \delta}\psi_{c,j}(r,R) - \frac{|P(r-R)|^2}{|P(r-R)|^2 + \delta}O_{g,j}(r)\right)$$

Without loss of generality we consider application of the above rewritten equation 17 when there are n aperture positions and we want to undertake i iterations.

In embodiments of the present invention, an intermediate object function guess after j steps for aperture positions in the m$^{th}$ region $\tilde{O}_{g,m,j}$ is calculated in the same way as shown in FIG. 3 for aperture positions in the m$^{th}$ region. To calculate the intermediate object function for each region, the object function result from the previous iteration $\tilde{O}_{g,m,1} = O_{g,i}$ is utilised. For a first iteration of the algorithm, the object function may equal unity at all points r, or may be randomly chosen at each point. Other initial values may also be used. Further, it will be noted that the initial object function for each region may be equal, or may be different in value.

Thus, the intermediate object function $\tilde{O}_{g,m,j}$ is updated for the m$^{th}$ region using:

$$\tilde{O}_{g,m,j+1}(r) = \tilde{O}_{g,m,j}(r) + \qquad (18)$$
$$w(r-R)\left(\frac{P^*(r-R)}{|P(r-R)|^2 + \delta}\psi_{c,j}(r,R) - \frac{|P(r-R)|^2}{|P(r-R)|^2 + \delta}\tilde{O}_{g,m,j}(r)\right)$$

wherein $$j \in 1, \ldots, \frac{n}{m} - 1, R = R_{f(j)}$$

wherein f(j)=mod(j,n), where mod represents the modulus (remainder) of j after integer division by n.

If n/m is not an integer then a maximum value of j may be chosen appropriately. For example, in an example embodiment comprising 2 regions and 5 aperture positions (m=2, n=5), one region would necessarily comprise 3 aperture positions, whilst the other comprises 2 aperture positions. For the region comprising 3 aperture positions, j would need to assume values of 1, 2 and 3, whilst for the other region j would need to assume values of 1 and 2. Therefore, the maximum value of j for each region should be chosen appropriately.

As a result of step 405, intermediate object function guesses for all of the regions have been calculated. Thus for the example, after the first step j=1 there has been calculated $\tilde{O}_{g,1,1}$ which is the intermediate object function guess for region 1 and $\tilde{O}_{g,2,1}$ for region 2.

In step 406, the intermediate object function guesses are combined to produce an object function guess $O_{g,i}$ for iteration i.

Combination of intermediate function guess can be achieved by:

$$O_{g,i+1} = O_{g,i} + \frac{W_t(r)}{\max(W_t(r))}\left(\sum_{k=1,\ldots,m} w_S(r, S_k)\tilde{O}_{g,k,n/m}(r) - O_{g,i}\right) \qquad (19)$$

where max($W_t$(r)) is the maximum value of $W_t$(r) over r.

In step 407 it is determined whether the algorithm has been iterated a sufficient number of times. The algorithm may proceed for a pre-determined number of iterations, for example 1000, or alternatively can be terminated when the sum squared error (SSE) is sufficiently small.

The SSE can be computed as:

$$SSE = \frac{\sum\left(\left|\sum_{k=1,\ldots,m} w_S(r, S_k)\tilde{O}_{g,k,n/m}(r)\right|^2 - |O_{g,i}|^2\right)}{N} \qquad (20)$$

where N is the numbers of pixels in O.

Testing has shown that the above-described prior art solution requiring 85 seconds per iteration has been reduced using certain embodiments of the present invention to 5 second per iteration when using an Intel® Core2 PC.

A second embodiment of the present invention will now be described wherein the partitioning of aperture positions amongst regions is frequently changed.

In the second embodiment, shown in FIG. 7, aperture positions are reassigned amongst regions during iterations of computation of the object function. The assignment of aperture positions does not have to be fixed for all iterations of the algorithm. For example, the assignment of aperture positions may be changed after 50% of the iterations have been performed, or after every 10% or 25% of the iterations. More preferably, the aperture positions may be reassigned amongst the regions for every iteration of the algorithm. The assignment of aperture positions to regions may be performed on a predetermined or random basis.

The method begins in step 701 and in step 702 a weighting function for each aperture position is calculated. The weighting function for each aperture may be calculated in advance, as previously discussed. In step 703, an initial partitioning of aperture positions amongst a plurality of regions is performed. The initial partitioning may be predetermined, in which case it would allow the calculation of initial weighting functions for each region to also be calculated in advance. In step 705, calculation of intermediate objection functions is assigned amongst computational units, as in step 404 of the first embodiment. In step 706 a first calculation of an intermediate object function is performed in parallel for each of the regions. The intermediate object functions are then combined in step 707 to form an object function for the first iteration. In step 707, the aperture positions are reassigned amongst the regions. Thus in the previously mentioned example, region S1 may comprise aperture positions $R_1$ and $R_3$ in the first iteration, which is then changed in step 708 to comprise aperture positions $R_1$ and $R_4$ in the second iteration. Due to the reallocation of aperture positions, weighting functions for the regions are recalculated in step 709. If a predetermined reassignment of aperture positions to regions is utilised, the reassigned weighting functions may be calculated in advance and stored in memory for use in step 709. In step 710, intermediate object functions are calculated for each of the regions, which are then combined in step 711 to form an object function guess for that iteration. In step 712, it is determined whether enough iterations have been performed in the same way as in step 407 in the first embodiment. Although FIG. 7 shows aperture positions being reassigned amongst regions for every iteration, the second embodiment is not constrained in this way and reassignment may be performed as desired.

An advantage of the calculation of intermediate object functions for each region which are then combined to produce an object function for that iteration is that the a level of interdependency between intermediate object functions and a combined object function is introduced, reflecting the actual interdependence between regions in the real object. For example, if intermediate object functions for each region were calculated by 1000 iterations of equation 18, then the intermediate object functions for each region combined to produce a final object function, disparities, seen as, for example, a large difference between object functions for each region could exist. However, frequent combination of the intermediate object functions for to produce a combined object function reduces such differences. That is, the intermediate object functions are combined and the combination used in a subsequent iteration for calculating each intermediate object function, thus avoiding each intermediate function being created in isolation.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A computer-based method for providing image data of a region of a target object, comprising the steps of:
   estimating by a first computational unit a first intermediate object function indicating at least one characteristic of a first sub-region of said region of the target object;
   estimating by a second computational unit a second intermediate object function indicating at least one characteristic of a second sub-region of said region of the target object;
   wherein each sub-region of said region of the target object comprises information relating to one or more selected areas of the target object, and the first and second intermediate object functions are estimated by the first and second computational units at least in part in parallel;
   determining a weighting factor for each selected area of the target object based upon a relative amplitude of a probe function for the respective area; and
   combining at a computation unit the first and second intermediate object functions to form a combined object function indicating at least one characteristic of the region of the target object.

2. The computer-based method of claim 1, comprising transferring at least one intermediate object function from the first or second computational units to combine with at least one other intermediate object function.

3. The computer-based method of claim 1, comprising estimating further intermediate object functions, each relating to a further sub-region of the target object, wherein the further intermediate object functions are combined with the first and second object functions to form the combined object function.

4. The computer-based method of claim 3, wherein the number of intermediate object functions is predetermined.

5. The computer-based method of claim 1, wherein the areas of the target object are selected by either re-positioning incident radiation or an aperture relative to the target object.

6. The computer-based method of claim 1, comprising allocating the selected areas of the target object amongst the sub-regions.

7. The computer-based method of claim 6, wherein the areas of the target object are allocated amongst the sub-regions such that each sub-region comprises an equal number of areas.

8. The computer-based method of claim 7, comprising reallocating the areas of the target object amongst the sub-regions.

9. The computer-based method of claim 1, comprising iteratively re-estimating said intermediate object functions, whereby the accuracy of a running estimate of the combined object function is improved with each iteration.

10. The computer-based method of claim 9, wherein said re-estimation of said intermediate object functions is based upon the combined object function from a previous iteration.

11. The computer-based method of claim 9, comprising terminating the iteration process when a predetermined event occurs.

12. The computer-based method of claim 11, wherein said predetermined event comprises the number of iterations satisfying a predetermined condition.

13. The computer-based method of claim 11, wherein said predetermined event comprises the sum squared error satisfying a predetermined condition.

14. The computer-based method of claim 9, wherein intermediate object functions are combined for a i+1th iteration according to:

$$O_{g,i+1} = O_{g,i} + \frac{W_t(r)}{\max(W_t(r))}\left(\sum_{k=1,\ldots,m} w_S(r, S_k)\tilde{O}_{g,k,n/m}(r) - O_{g,i}\right)$$

where $O_{g,i}$ is a combined object function for an $i^{th}$ iteration, m is a number of sub-regions, ws(r,Sk) is a weighting factor for a sub-region $S_k$, $\tilde{O}_{g,k,n\ l\ m}$ is an intermediate object function guess for a $k^{th}$ sub-region for n/m steps, max($W_t$(r)) is the maximum value of $W_t$(r) over r.

15. The computer-based method of claim 1, comprising determining a weighting factor for each of the sub-regions, wherein the plurality of intermediate object functions are combined according to the respective weighting factor for the sub-regions.

16. The computer-based method of claim 1, wherein a weighting factor for each sub-region is based upon the weighting factors for the selected areas allocated to each sub-region.

17. The computer-based method of claim 16, wherein the weighting factor for each sub-region is re-determined following reallocation of selected areas to that sub-region.

18. The computer-based method of claim 1, wherein estimating each intermediate object function comprises:
  multiplying the object function by a probe function indicating at least one characteristic of incident radiation at said target object;
  providing an exit wave function responsive to a result of said multiplication;
  propagating the exit wave function to provide an estimate of an expected scattering pattern; and
  correcting at least one characteristic of said expected scattering pattern according to a detected intensity.

19. The computer-based method of claim 1, comprising updating each intermediate object function for a j+1th step according to:

$$\tilde{O}_{g,m,j+1}(r) =$$
$$\tilde{O}_{g,m,j}(r) + w(r-R)\left(\frac{P^*(r-R)}{|P(r-R)|^2 + \delta}\psi_{c,j}(r, R) - \frac{|P(r-R)|^2}{|P(r-R)|^2 + \delta}\tilde{O}_{g,m,j}(r)\right)$$

wherein $\tilde{O}_{g,m}$(r) is an intermediate object function for a $j^{th}$ step, $$j \in 1, \ldots, \frac{n}{m} - 1$$

wherein n is a number of selected areas, m is a number of sub-regions, w(r–R) is a weighting function for a selected area j, P(r–R) is a probe function at a position R, P*(r–R) is the conjugate of the probe function P(r–R), $\Psi_{c,j}$(r,R) is a corrected guess at an exit wave function for area j and δ is a selectable parameter.

20. The computer-based method of claim 19, wherein $\tilde{O}_{g,m}$(r) corresponds to a previous combined object function $O_{g,i}$.

21. A non-transitory computer-readable data storage medium having instructions stored thereon which, when executed by a computer, perform the method of claim 1.

* * * * *